United States Patent [19]

LaBombard

[11] Patent Number: 4,817,598
[45] Date of Patent: Apr. 4, 1989

[54] TRACHEOSTOMY TUBE WITH RING PULL REMOVABLE INNER CANNULA

[75] Inventor: Denis LaBombard, Georgetown, Mass.

[73] Assignee: Portex, Inc., Wilmington, Mass.

[21] Appl. No.: 59,078

[22] Filed: Jun. 8, 1987

[51] Int. Cl.[4] ............................................. A61M 16/00
[52] U.S. Cl. ................................................ 128/207.14
[58] Field of Search ...................... 128/207.14, 207.15, 128/200.26, 207.16, 207.17; 604/158, 165

[56] References Cited

U.S. PATENT DOCUMENTS

| | | | |
|---|---|---|---|
| 2,765,792 | 10/1956 | Nichols | 128/200.26 |
| 3,088,466 | 5/1963 | Nichols | 128/200.26 |
| 3,169,529 | 2/1965 | Koenig | 128/207.14 |
| 3,263,684 | 8/1966 | Bolton | 128/207.15 |
| 3,334,631 | 8/1967 | Stebleton | 128/200.26 |
| 3,587,589 | 6/1971 | Eb32 | 128/207.14 |
| 3,659,612 | 5/1972 | Shiley et al. | 128/207.15 |
| 3,688,774 | 9/1972 | Akiyama | 128/207.15 |
| 3,731,692 | 5/1973 | Goodyear | 128/207.15 |
| 3,889,688 | 6/1975 | Eamkaow | 128/207.14 |
| 3,948,273 | 4/1976 | Sanders | 128/207.15 |
| 3,973,569 | 8/1976 | Sheridan et al. | 128/207.14 |
| 3,987,798 | 10/1976 | McGinnis | 128/207.15 |
| 4,009,720 | 3/1977 | Crandall | 128/207.15 |
| 4,033,353 | 7/1977 | La Rosa | 128/207.15 |
| 4,045,058 | 8/1977 | Eross | 128/207.14 |
| 4,235,229 | 11/1980 | Rauford et al. | 128/207.15 |
| 4,315,505 | 2/1982 | Crandall et al. | 128/207.15 |
| 4,471,776 | 9/1984 | Cox | 128/207.15 |
| 4,593,690 | 6/1986 | Sheridan et al. | 128/207.15 |

FOREIGN PATENT DOCUMENTS 125754  11/1919  United Kingdom ............ 128/200.26

Primary Examiner—Edward M. Coven
Assistant Examiner—J. P. Lacyk
Attorney, Agent, or Firm—Pollock, Vande Sande & Priddy

[57] ABSTRACT

A removable inner cannula is provided with grooved-ribbed locking member end for snap-fit interconnection inside an outer cannula. The inner cannula includes a ring-pull grasping member associated with the locking member which is easily accessible for withdrawal of the inner cannula from the outer cannula connection.

7 Claims, 1 Drawing Sheet

U.S. Patent   Apr. 4, 1989   4,817,598
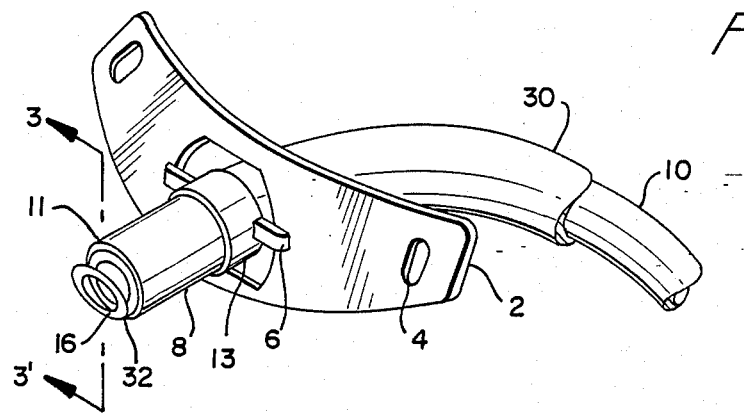
FIG 1
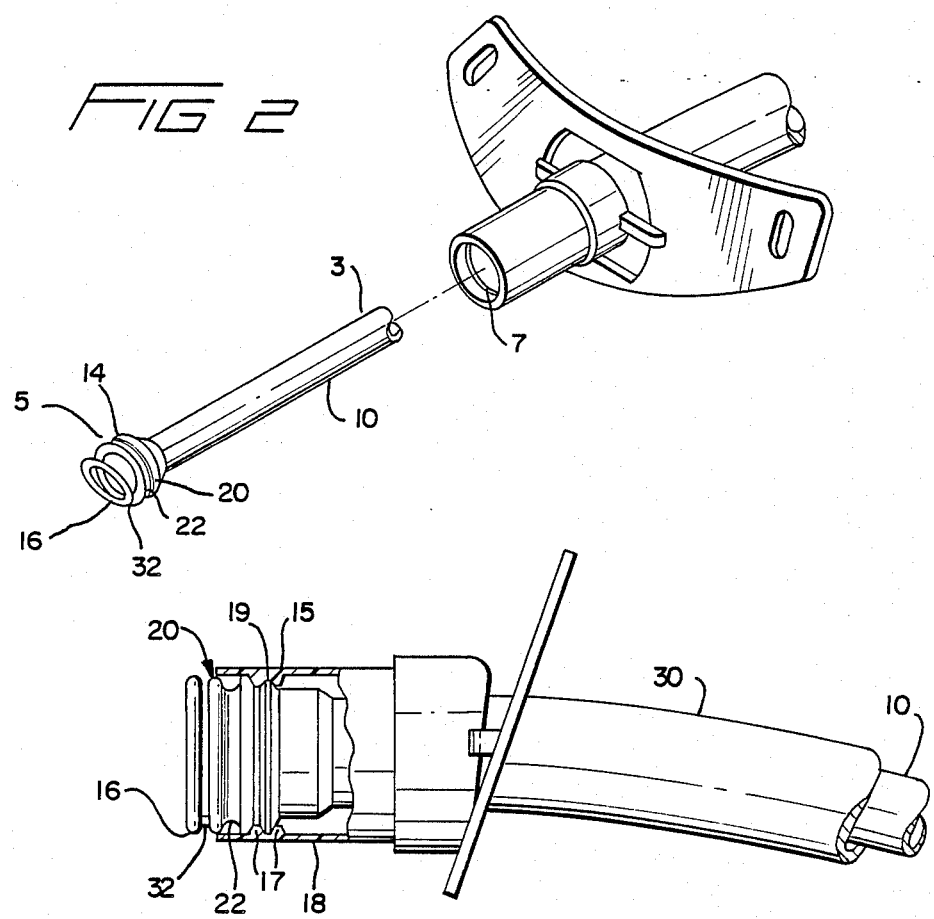
FIG 2
FIG 3

TRACHEOSTOMY TUBE WITH RING PULL REMOVABLE INNER CANNULA

BACKGROUND OF THE INVENTION

The present invention relates to respiratory circuits and particularly to tracheostomy tubes comprising of an outer constant radius cannula and a removable inner cannula.

Tracheostomy tubes with removable inner cannula are well known in the prior art. When a two part tracheostomy tube is placed in the patients trachea, if the patients tracheostomy should become occluded by mucus or phlegm, the tracheostomy tube airway can be cleaned by removing the inner cannula. After being cleaned, the inner cannula can be placed inside the outer cannula of the tracheostomy tube which remains in place in the trachea.

Various means of connecting the inner cannula to the tracheostomy tube and connecting the tracheostomy tube to a ventilation system and the like are also well known. Examples showing various connecting means are: U.S. Pat. No. 3,088,466 to Nichols; U.S. Pat. No. 3,659,612 to Shiley, et al.; U.S. Pat. No. 4,009,720 to Crandall, et al.; and U.S. Pat. No. 4,315,545 to Crandall, et al., also assigned to Shiley. All of these patents show various means for interconnecting the inner cannula and the outer tracheostomy tube cannula by means of a coupling connector. It is common for all of these patents, that the coupling connecting means to the ventilator or the like is integral with or connected to the removable inner cannula and that an additional connection is required between the outer tracheostomy tube cannula and the body of the inner cannula.

Tracheostomy tubes of this design have several disadvantages. First, they require an additional disconnection point between the outer and inner cannula which reduces the safety of the system. Such prior art tracheostomy tube devices must have an air tight seal between the inner and outer cannulae and at the ventilator connecting means which is typically part of the inner cannula.

Second, the need exists in the art to improve the security of the respiratory system so that the accidental disconnection of the parts of the tracheostomy tube assembly can be prevented. At the present time there is no interconnecting system in the respiratory art that can provide high security for the connection of an inner cannula within a respiratory circuit.

Third, the need has been emphasized for some time to provide a system which will only be disconnectable at the ventilator connecting means. The problem is discussed in a study by Arthur D. Little entitled: "Accidental Disconnection of Breathing Circuits". The current state of the art tracheostomy devices, by design and preferred embodiment, require an additonal disconnection point which reduces the safety of the patient. The preferred embodiment of the present invention, proposes to overcome the above discussed disadvantages of the prior art.

According to the preferred embodiment of the present invention, the ventilator circuit is provided with a tracheostomy tube having a ventilator connection means integral to the outer tracheostomy tube cannula, and a removable inner cannula tube made separately from the outer cannula and placeable inside the outer cannula and the ventilator connection means. This design enhances the safety of the respiratory air delivery system. The removable inner cannula is safely placed inside the connector while the device is attached to various ventilator connection means such as elbows, swivels, connectors, etc. minimizing the possibility of unintentional disconnection.

SUMMARY OF THE PRESENT INVENTION

The purpose of this invention is to provide a tracheostomy tube with a removable inner cannula adapted for placement inside the ventilation delivery system which will enhance the safety of the connection of the tracheostomy tube by eliminating a possible disconnection point between the inner and outer cannulae at the connector site.

Another purpose of the present invention is to provide a means for facilitating removal of an inner cannula from the ventilator coupling connector member of the outer tracheostomy cannula.

Still another purpose of this invention is to provide a system allowing easy and dependable interconnecting of the inner cannula within the ventilator coupling connector body without the necessity for using a sealing means between the outer cannula, the inner cannula and/or the ventilator connector member.

Yet another important purpose of the present invention is to provide the device which would accomplish the above functions with a simple and inexpensive structure.

To this end, the present preferred embodiment of the removable inner cannula is placed inside the air delivery path of the tracheostomy tube with locking means at its proximal end adapted for snap-fit interconnection into the tracheostomy tube ventilator connector member. The locking means are also provided with a grasping means for facilitating withdrawal of the inner cannula from the connector member.

BRIEF DESCRIPTION OF THE DRAWINGS

The preferred embodiment of the present invention device will now be described in more detail with reference being made to the drawings in which:

FIG. 1 shows a perspective view of the removable inner cannula according to the present invention inserted into the connector member.

FIG. 2 shows the embodiment shown in FIG. 1 with removable inner cannula withdrawn from the connector.

FIG. 3 shows cross-section taken along lines 3' of FIG. 1.

DETAILED DESCRIPTION OF THE PREFERRED EMBODIMENT

Referring first to FIG. 2 the inner cannula tube 10 is shown withdrawn from the tubular connector member 8. As clearly appears from FIG. 2 the inner cannula 10 is made as a part separate from the tubular connector member 8. The inner cannula has a first end 3 and a second end 5. The first end 3 is insertable through the opening 7 in the circular connector member 8 into an outer tube 30. The outer tube 30 of the tracheal system can be permanently connected to the connector member 8 or made integral with the connector. The inner cannula tube 10 includes a ribbed-grooved member 14 provided at it second end 5. Member 14 is inserted onto the outer wall of tube 10 and includes a plurality of ring-like ribs 20 forming grooves 22 therebetween. The exterior ring-like rib defining annular ring 16 is partially cut around the major portion of its circumference and is connected to other ribs 20 with hinge means 32.

As clearly shown in FIG. 2 the exterior annular ring 16 forms a ring-pull feature constituting a grasping means. The ring annular 16 can be folded integrally with the remaining portion of the member 14 and can be easily grasped with the fingers to facilitate removal of the inner cannula 10 from the connector member 8. As shown in FIG. 1 the grasping means of the inner cannula member is extending beyond the connector member 8 when the inner cannula 10 is fitted into the connector member and is easily reachable for removal of the inner cannula. At the same time, the ring-pull feature takes a minimum of space inside the coupling connector. The ribbed-grooved member 14 in the preferred embodiment is made from a flexible plastic polymeric material.

The removable inner cannula is adapted for interlocking into the connector body through the ribbed-grooved member 14. As better shown in FIG. 3 the connector member 8 at its first end 11 includes first locking means 15 on the interior wall of the connector member 8 for interacting with the member 14 which defines second locking means of the inner cannula 8. This first locking member 15 includes at least a pair of circular ribs 17 forming a groove 19 therebetween and adapted for snap-fit connection with corresponding second locking member comprising ribbed-grooved member 14. A presence of the definite snap-fit provides simple but dependable indication that the inner cannula device is in place within a connector member.

Placement of the removable inner cannula inside the connector member within the air delivery system is very advantageous. It reduces the possibility of accidental disconnection between inner and outer cannulae. When the respirator connection is made to the tracheostomy device, the plastic deformation of the connector member provides additional clamping force holding the inner cannula in place.

The tracheostomy assembly according to the present invention allows therefore to dispense with any conventional sealing means necessary for known tracheostomy tubes having removable inner cannula.

The degree of safety of the present invention tracheostomy device is superior in comparison with prior art devices since the coupling connector 8 is always available for connection to a respirator circuit with or without inner cannula 10 being placed inside the outer tube.

The inner cannula of the present invention is described in the preferred embodiment in connection with tracheostomy assemblies using 15 mm and 22 mm coupling connector. However, the locking and grasping features described here in connection with the inner cannula can be used in many other applications. It can for example be utilized with replaceable filter systems attached to the ring pull feature and bacterial filters, moisture devices, and any type of device which could utilize the fold out ring for facilitation of its removal from an internal snap-fit or tempered locking device.

The connector 8 used with the removable inner cannula 10 is provided with a flange 2 which is made of a flexible material and attached to the opposite end 13 of the connector 8 with the pair of flexible pivot webs 6 molded to both the connector 8 and the flange 2. The webs 6 increase the flexibility of the flange 2 and provide for better comfort of the patient without the possibility of disconnection between the flange member 2 and the connector 8. The flange 2 can be made as a single piece molded flange including the webs 6.

In the preferred embodiment, the connector member 8 is designed as an angular offset which lowers the position of the attaching apparatus from the upper neck and chin area. Two tape slots 4 are provided in the flange member 2. The tape slots 4 are of a size sufficient to allow a full size half inch type tape to be easily threaded through the flange. The slots 4 will provide a high degree of flexibility to the system as well as guard against abrasion of the tape on the neck area. The provision of two flexible webs 6 and a large opening between the connector and the flange walls allows significantly larger open area around the stoma site and provide full view of the stoma for proper maintenance.

What is claimed is:
1. A removable cannula system comprising:
an outer cannula having a first and second end;
an inner cannula having a first and second end, said inner cannula being interconnectable inside said outer cannula at said second ends;
first locking means disposed inside said outer cannula at said second end and second locking means disposed at said second end of said inner cannula for interconnecting said inner cannula inside said outer cannula; and,
grasping means for facilitating withdrawal of said inner cannula from said outer cannula, said grasping means including an annular ring with a hinge means connecting said annular ring to said inner cannula, said annular ring being alignable with an opening of said outer cannula at said second end and easily accessible to the fingers to be unfolded for pulling said inner cannula from said outer cannula.

2. A removable cannula system according to claim 1 wherein said second locking means includes a plurality of ribbed-grooved members on said inner cannula and said first locking means includes at least a pair of corresponding ribs forming a groove therebetween on an inner wall of said outer cannula adapted for snap-fit interconnection with at least one of said ribbed-grooved members of said second locking means.

3. A removable inner cannula according to claim 2 wherein said hinge means connects said annular ring to said second locking means.

4. A tracheostomy tube comprising:
an outer cannula having a first and second end;
a tubular connector member integral with said outer cannula at said second end;
a removable inner cannula removably disposed inside said outer cannula, said inner cannula having a first and second end, said inner cannula being interlockable inside said connector member at said second end;
first locking means disposed inside said tubular connector member and second locking means disposed at said second end of said inner cannula for interconnecting said inner cannula inside said connector member; and
grasping means for facilitating withdrawal of said inner cannula from said outer cannula, said grasping means including an annular ring with a hinge means connecting said annular ring to said inner cannula, said annular ring being alignable with an opening of said tubular connector member and easily accessible to the fingers to be unfolded for pulling said inner cannula from said outer cannula.

5. A tracheostomy tube according to claim 4 wherein said second locking means includes a plurality of ribbed-grooved members on said inner cannula tube and said first locking means includes at least a pair of corresponding ribs forming a groove therebetween on an inner wall of said outer cannula adapted for snap-fit interconnection with at least one of said ribbed-grooved members of said second locking means.

6. A tracheostomy tube according to claim 5 wherein a diameter of said annular ring substantially corresponds to the diameter of the ribs of said locking means.

7. A tracheostomy tube according to claim 2 wherein a diameter of said annular ring substantially corresponds to the diameter of the ribs of said second locking means.

* * * * *